(12) United States Patent
Kosecoff et al.

(10) Patent No.: US 12,280,271 B2
(45) Date of Patent: Apr. 22, 2025

(54) HAIR TREATMENT SYSTEM WITH PROXIMITY SENSORS TO DETECT SCALP OR HAIR DISTANCE AND LOCALITY

(71) Applicant: L'Oreal, Paris (FR)

(72) Inventors: David B. Kosecoff, San Francisco, CA (US); Florent Valceschini, Jersey City, NJ (US); Dominic Akerele, Brooklyn, NY (US); Nicholas Sinclair, Brooklyn, NY (US)

(73) Assignee: L'Oreal, Paris (FR)

( * ) Notice: Subject to any disclaimer, the term of this patent is extended or adjusted under 35 U.S.C. 154(b) by 112 days.

(21) Appl. No.: 17/025,598

(22) Filed: Sep. 18, 2020

(65) Prior Publication Data
US 2022/0088407 A1 Mar. 24, 2022

(51) Int. Cl.
*A61H 9/00* (2006.01)
*A61N 5/06* (2006.01)

(52) U.S. Cl.
CPC ......... *A61N 5/0617* (2013.01); *A61H 9/0071* (2013.01); *A61H 2201/10* (2013.01); *A61H 2201/5058* (2013.01); *A61H 2205/021* (2013.01); *A61N 2005/0626* (2013.01); *A61N 2005/0643* (2013.01); *A61N 2005/0651* (2013.01)

(58) Field of Classification Search
CPC .......... A61N 5/0617; A61N 2005/0626; A61N 2005/0643; A61N 2005/0651; A61H 9/0071; A61H 2201/10; A61H 2201/5058; A61H 2205/021
See application file for complete search history.

(56) References Cited

U.S. PATENT DOCUMENTS

| | | | |
|---|---|---|---|
| 2,074,481 A | 3/1937 | Macmullen et al. | |
| 2005/0081871 A1 | 4/2005 | Ramet | |
| 2006/0076030 A1* | 4/2006 | De Laforcade | A45D 19/026 132/142 |
| 2007/0038206 A1* | 2/2007 | Altshuler | A46B 15/0036 606/20 |

(Continued)

FOREIGN PATENT DOCUMENTS

| | | | |
|---|---|---|---|
| CN | 101254045 B | * 3/2013 | ............. A45D 19/02 |
| CN | 209801823 U | * 12/2019 | |

(Continued)

OTHER PUBLICATIONS

Invitation to Pay Additional Fees and Annex, Communication Relating to the Results of the Partial International Search mailed Nov. 15, 2021, in corresponding PCT Application No. PCT/US2021/050966, filed Sep. 17, 2021, 17 pages.

(Continued)

*Primary Examiner* — Carl H Layno
*Assistant Examiner* — Aya Ziad Bakkar
(74) *Attorney, Agent, or Firm* — Christensen O'Connor Johnson Kindness PLLC (57) ABSTRACT

A device comprises a treatment system to treat scalp or hair; one or more sensors configured to detect at least one spatial condition selected from device contact with scalp or hair, device distance to scalp or hair, and device location in relation to scalp or hair; a controller configured to send instructions to adjust the treatment system based on the detected spatial condition of the device.

15 Claims, 7 Drawing Sheets

(56) References Cited

U.S. PATENT DOCUMENTS

| | | | |
|---|---|---|---|
| 2011/0308034 A1 | 12/2011 | Powers et al. | |
| 2013/0184693 A1* | 7/2013 | Neev | A61N 5/0616 |
| | | | 606/9 |
| 2014/0088522 A1 | 3/2014 | Nuzzo et al. | |
| 2015/0189980 A1 | 7/2015 | Hwang et al. | |
| 2017/0150810 A1 | 6/2017 | Brewer et al. | |
| 2017/0326020 A1 | 11/2017 | Caberlotto et al. | |
| 2019/0098977 A1 | 4/2019 | Thiebaut et al. | |
| 2019/0209077 A1* | 7/2019 | Charraud | A61B 5/0077 |
| 2019/0209078 A1 | 7/2019 | Charraud et al. | |
| 2020/0196937 A1* | 6/2020 | Gopalan | A45D 44/005 |
| 2020/0202520 A1 | 6/2020 | Joyce et al. | |

FOREIGN PATENT DOCUMENTS

| | | | | |
|---|---|---|---|---|
| EP | 1472955 A1 * | 11/2004 | | A45D 1/00 |
| GB | 2569655 A * | 6/2019 | | A45D 1/00 |
| JP | S61188503 U | 11/1986 | | |
| JP | 2001275737 A | 10/2001 | | |
| JP | 2007526804 A | 9/2007 | | |
| JP | 2010131260 A | 6/2010 | | |
| WO | 2018/164905 A1 | 9/2018 | | |
| WO | 2018/224639 A1 | 12/2018 | | |
| WO | 2019136232 A1 | 7/2019 | | |

OTHER PUBLICATIONS

International Preliminary Report on Patentability, mailed Mar. 30, 2023, in corresponding International Patent Application No. PCT/US2021/050966, 16 pages.

Notification of Reasons for Refusal for JP App. No. 2023-517960 dated Dec. 14, 2023.

Communication pursuant to Article 94() EPC for for EP Pat. App. 21782623.9 dated Mar. 5, 2024. 11 pages.

Chinese Office Action mailed Oct. 31, 2024, issued in related Chinese Application No. 202180077862.2 filed Sep. 17, 2021, 5 pages.

Office Action for EP Pat. App. No. 21782623.9, dated Sep. 10, 2024. 6 pages.

Office Action dated May 6, 2024 for CN Patent Application No. 2021800778622. 7 pages.

Office Action dated Jul. 26, 2024, issued for Korean Pat. App. No. 10-2023-7012473 filed Sep. 17, 2021.

* cited by examiner

HAIR TREATMENT SYSTEM WITH PROXIMITY SENSORS TO DETECT SCALP OR HAIR DISTANCE AND LOCALITY

SUMMARY

In one embodiment, a hair treatment system intelligently treats or diagnoses hair and scalp by region. In one embodiment, proximity sensors, such as a camera or infrared (IR) or both camera and infrared sensors in conjunction with contact sensors are used to approximate distance and locality and to generate commands that modify a dispensing or diagnosing product along length of hair and into the scalp.

In one embodiment, the hair treatment system facilitates pattern applications and treatment dosages (e.g. roots vs ends of hair) as well as differentiating scalp from hair from air.

In one embodiment, the hair treatment system controls outflow or direction of scalp and hair treatments so as to minimize waste and inhalable mists.

In one embodiment, the hair treatment system includes a scalp contact sensor, for example, open or short detectors or dielectric sensors on bristle tips of brushes or combs, and determines whether or not the hair treatment system is in contact proximity of the scalp or hair roots.

In one embodiment, the location on the head (top vs sides) is further calculated through the use of an accelerometer. A camera and/or IR sensor determines how far the device is from the scalp, whether it is in contact with hair, and whether it has reached the ends of the hair. Different types of product are dispensed (i.e. by way of nozzles or spray valves) and or different types of LED's are illuminated (i.e. Red vs UV) according to the different regions on the hair or scalp.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A number of scalp and hair treatment devices are known. For example, reference can be made to the Applicant's prior publications 2005/0081871, 2014/0088522, 2017/0150810, 2017/0326020, 2019/0098977, 2019/0209077. According to the present disclosure, devices for treating the hair or scalp or both hair and scalp can be improved by including sensors that detect a precise location or proximity of the device in relation to the scalp and hair. A device with such sensors can use the information to control the treatment being delivered.

According to this disclosure, providing sensors renders more "intelligent" devices that can be programmed to adjust the treatment based on the location or proximity of the hair treatment device to the scalp or hair or whether the device is in actual contact with hair or scalp. Examples of hair and scalp treatment systems include, but are not limited to, scalp massagers, hair dryers, and dispensers for shampoo, bleach, coloring, and other formulations.

In one embodiment, a hair and scalp treatment system according to this disclosure is embodied in a hand-held, electrically powered device as illustrated in FIGS. 1 to 5. The device illustrated in the FIGURES is only an example of a hair or scalp treatment system. However, previously known hair and scalp treatment devices can also be modified to have the intelligent functionality described herein. For example, the device 100 shows comparatively large tines which can be used to dispense formulations, perform as a vacuum or blower, and provide light and electrostatic treatments. However, in other embodiments, the tines can be replaced with a brush-type head having bristles, such as the devices of US 2014/0088522, 2017/0150810, 2017/0326020, or a comb with teeth, such as the device of 2005/0081871.

In one embodiment, the device 100 is shaped in the style of well-recognized familiar hair appliances to inspire trust and confidence in the device leading to intuitive use and gestures when using the device.

Figure 3:
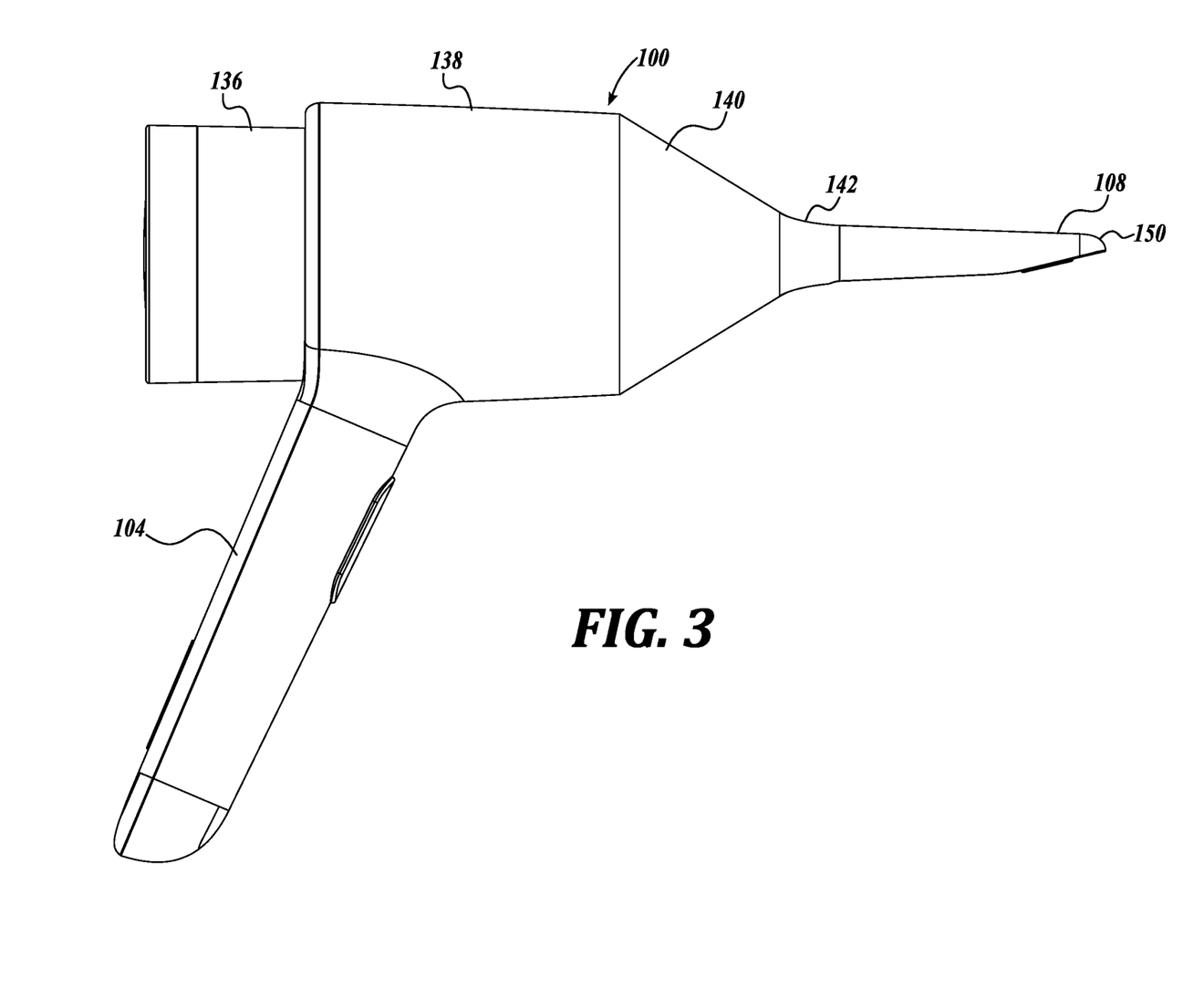
FIG. 3 is a diagrammatical illustration of a side view of the hair and scalp treatment device of FIG. 1.

Referring to FIG. 3, in one embodiment, the device 100 includes a handle 104 connected to the device 100 at the substantially cylindrical section 138. The handle 104 is connected to the device 100 at an obtuse angle with respect to the front end of the device 100. The handle 104 helps balance the device weight for more comfortable use.

Still referring to FIG. 3, at the back side, the device 100 can include a smaller diameter cylindrical shaped housing 136 that accepts a removable cartridge 102 containing a hair or scalp treatment formulation. The cartridge 102 can be configured to be a re-Tillable cartridge or a disposable cartridge. In one embodiment, the device 100 can be configured to hold more than one cartridges, wherein each cartridge can be filled with a different formulation for a different treatment.

Forward from the housing 136, the device 100 exterior shape increases step-wise to a larger outer diameter portion 138 compared to the housing 136 diameter. In one embodiment, the device 100 includes a body structure that has a substantially cylindrical or minimally tapered conical portion 138 from the back end to about the middle of the device length. In one embodiment, the handle 104 connects to the back side of portion 138. Then, proximally from the cylindrical or minimally conical portion 138, the device 100 takes on a more pronounced conical or decreasing elliptical shape 140 in the top to bottom plane (i.e., viewed from left or right side), from about the middle of the device 100 to about a third or fourth of the device length. However, in the side-to-side plane (i.e., viewed from top or bottom) the device 100 does not taper as much, since the device 100 is accommodating three tines in the side-to-side plane.

Then, distally from the smaller end of the conical or elliptical shape 140, the device 100 has a transition portion 142 that forms one or more dispensing tines 108 at the front end, so that each tine 108 is separate from the other tines. Although tines 108 are illustrated in connection with a hair or scalp treatment system, the device 100 can be configured as a brush or comb.

Figure 2:
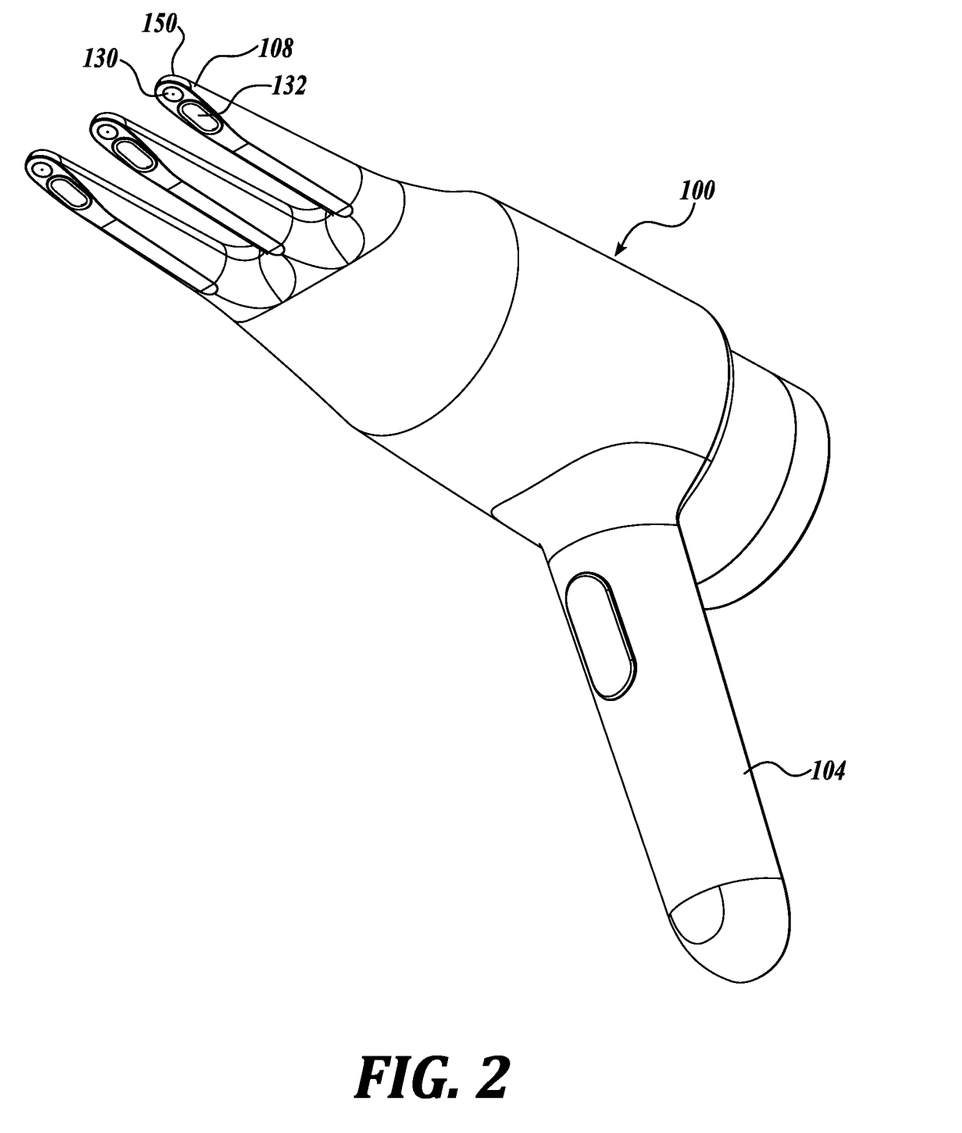
FIG. 2 is a diagrammatical illustration of the hair and scalp treatment device of FIG. 1.
Figure 5:
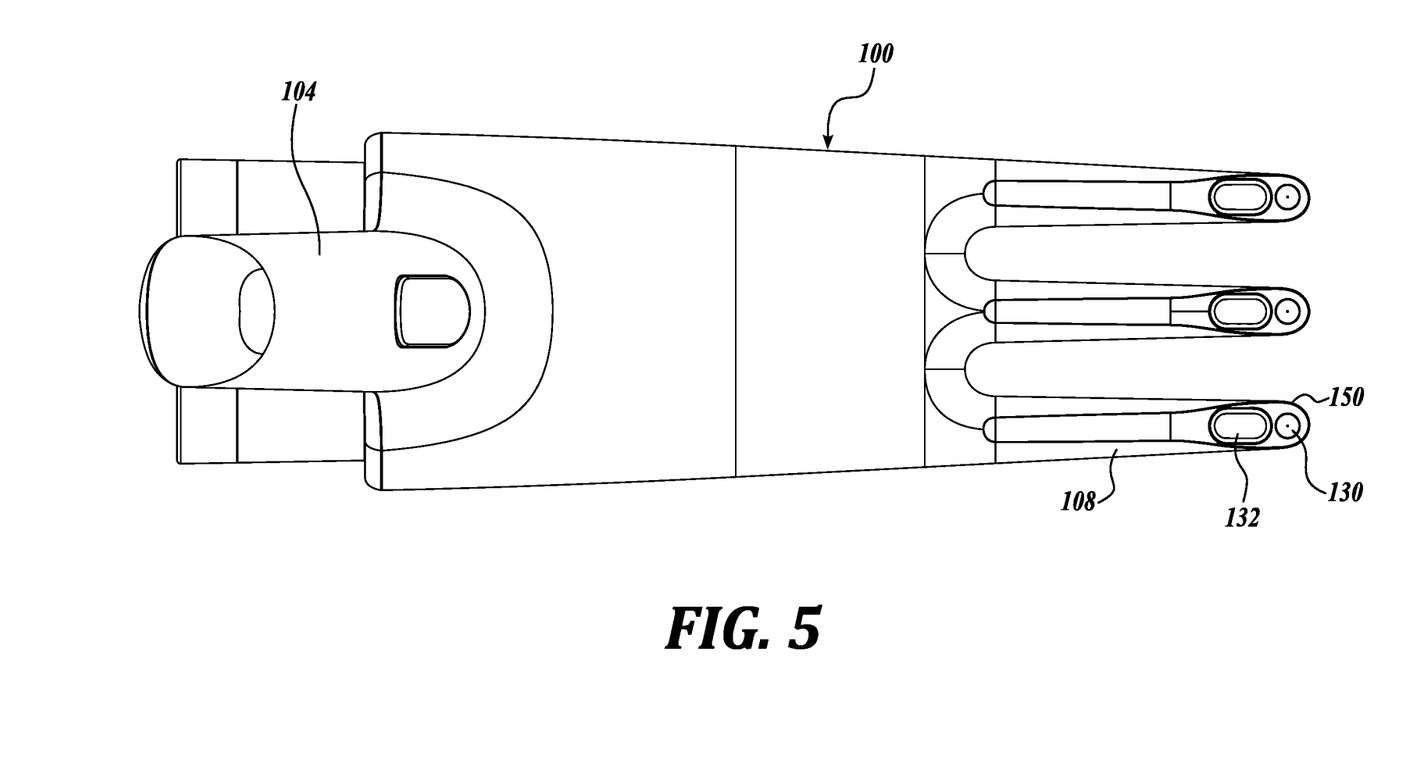
FIG. 5 is a diagrammatical illustration of a bottom view of the hair and scalp treatment device of FIG. 1.

Referring to FIGS. 2 and 5, each tine 108 has a gradually decreasing conical shape from the initial connection at the transition portion 142 section to the end of the tine 108 in both the side to side plane and the top to bottom plane.

In FIG. 5, the tines 108 are shown having a rounded tip when viewed from the bottom (or top) plane. However, in FIG. 3, the tines 108 are shown to have a flat area or chamfer at the bottom of the tine 108 at the front end when viewed from the side plane, resulting in a truncated rounded shape. The rounded tips of the tines 108 can part the hair for better access to the scalp and hair roots. The rounded tips of the tines include "agitation bumps" and the chamfered angle for cleansing and massaging action.

In FIG. 5, the chamfered section of the tines 108 has openings 130 for dispensing a formulation. In one embodiment, openings 130 can be static, meaning the spray or dispensing direction is set and cannot be adjusted. In one embodiment, the openings 130 can be directional, meaning the spray or dispensing direction can be controlled. For example, the openings 130 can be provided on a swivel ball that is controlled through micro-actuators. In one embodiment, multiple openings can be provided, wherein each opening is oriented in a different direction, and the formulation is dispensed from the selected opening in the preferred orientation. In one embodiment, controlling the direction of dispensing formulation allows also to apply the formulation in a pattern, such as back-and-forth "brushstroke" or circular patterns, for example. In one embodiment, the dispenser 112 can control the form in which the formulation is dispensed. For example, the formulation can be sprayed in different shaped patterns, such as flat fan versus cone, wide spray versus narrow, solid spray versus hollow, and stream versus mist. In one embodiment, the formulation is dispensed via adjustable conical nozzles that move forwards and backwards around a center stem to adjust the pattern of spray.

In one embodiment, the formulation can be dispensed as a liquid. In one embodiment, the formulation can be atomized and dispensed as a mist. Additionally, the chamfered section of tines 108 has openings 132 that lead to a vacuum system for collecting the used formulation with any debris or oils removed from the hair. In one embodiment, the openings 132 can be used for supplying heated air so that the device 100 functions as a hair drier.

In the illustrated embodiment, each tine 108 is shown having openings 130 for dispensing and openings 132 for vacuuming or blowing air. However, in one embodiment, there can be dedicated tines that only have openings for dispensing formulation and dedicated tines that only have openings used for vacuum or blowing. In one embodiment, there can be multiple openings on each tine 108 to provide for dispensing different formulations from the same tine. This can be advantageous where two formulations work together. In one embodiment, each opening can be dedicated to a different formulation. In one embodiment, the device 100 is provided with three tines 108 for even cleansing coverage. The angle of the handle 104 and the tine 108 length allows users to reach all areas of the scalp and hair.

In one embodiment, the device 100 includes an electrostatic treatment system. In one embodiment, the purpose of the electrostatic system is to charge a portion of the scalp or hair or both by induction or contact. In one embodiment, an electrode 150 is placed at the tips of the tines 108. The electrode 150 can also electrostatically charge the hair formulation droplets as they are dispensed from the openings 130. The charged hair formulation will then become attracted or repelled, according to the particular charges produced, to the target areas of the scalp or the hair. The electrode 150 is electrically connected to an electrostatic charger. In one embodiment, the electrode 150 may be surrounded by electrically insulation material.

In one embodiment, the device 100 can have multiple hair and scalp treatment systems. The device 100 is also provided with one or more sensors, including contact sensors, proximity sensors, accelerometers, and the like. The sensors provide input to a controller, which then controls the output of the one or more hair and scalp treatment systems based on the information provided by the sensors.

Figure 6:
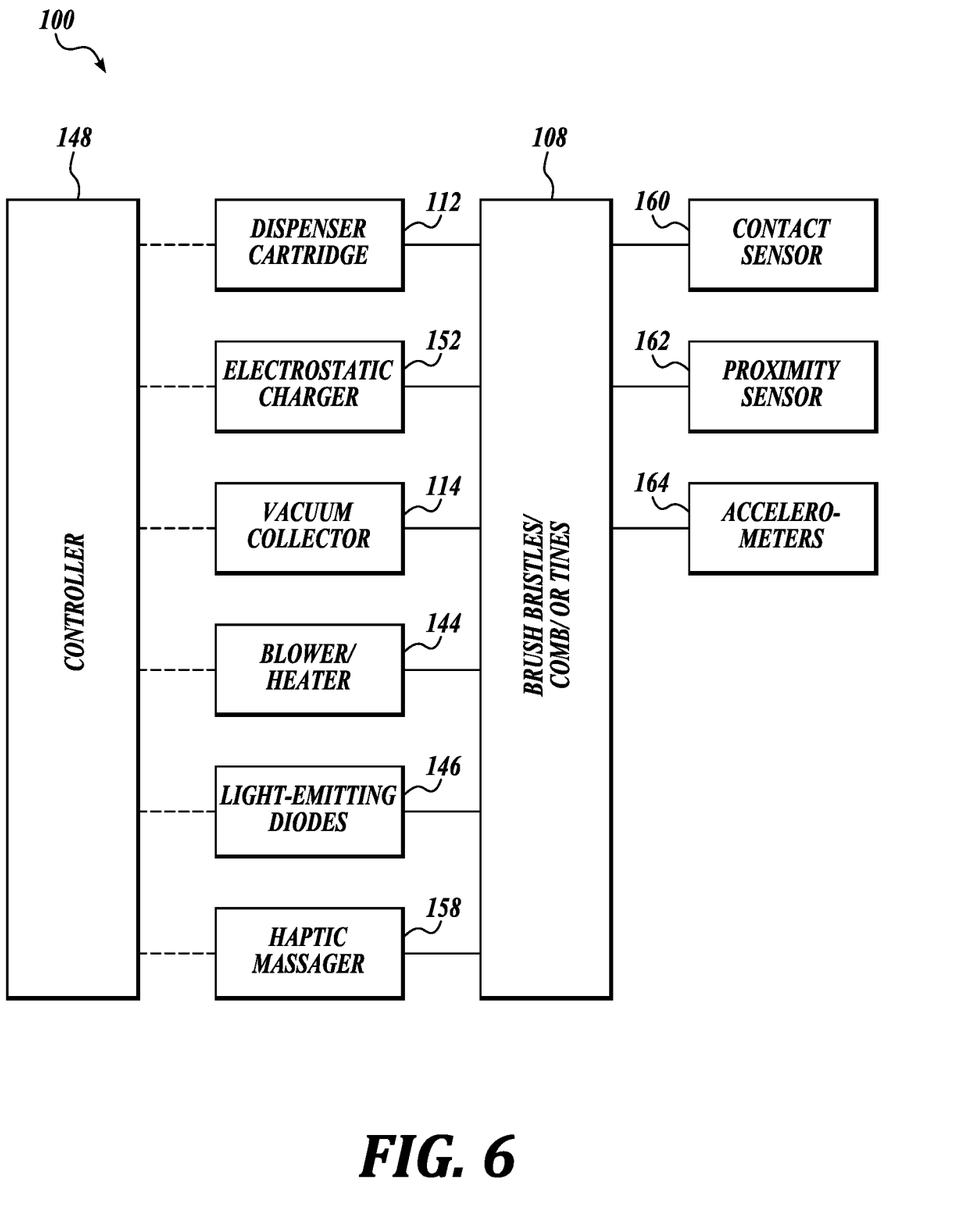
FIG. 6 is a schematic illustration of hair and scalp treatment systems that can be used with the device of FIG. 1.

Referring to FIG. 6, the device 100 is represented schematically to illustrate the use of sensors with the hair and scalp treatment systems. The device 100 can have one or more treatment systems including, but not limited to, a formulation dispenser 122, an electrostatic charger 152, a vacuum and collector system 114, a blower and heater system 144, a light treatment system 146, and a haptic vibrating massager 158. In one embodiment, the device 100 may include the above-mentioned treatment systems, only one of the treatment systems, or a combination of more than one treatment systems.

In one embodiment, the device 100 can be powered by alternating current (AC) or direct current (DC). In one embodiment, the device 100 is powered through common household alternating current that relies on an electrical cord (not shown) to supply power to the device 100. In one embodiment, the device 100 is powered through direct current, such as a rechargeable battery that can be charged by plugging into a household alternating current outlet. A direct current powered device 100 allows the device to be used without staying or standing in proximity to an electrical outlet.

Figure 1:
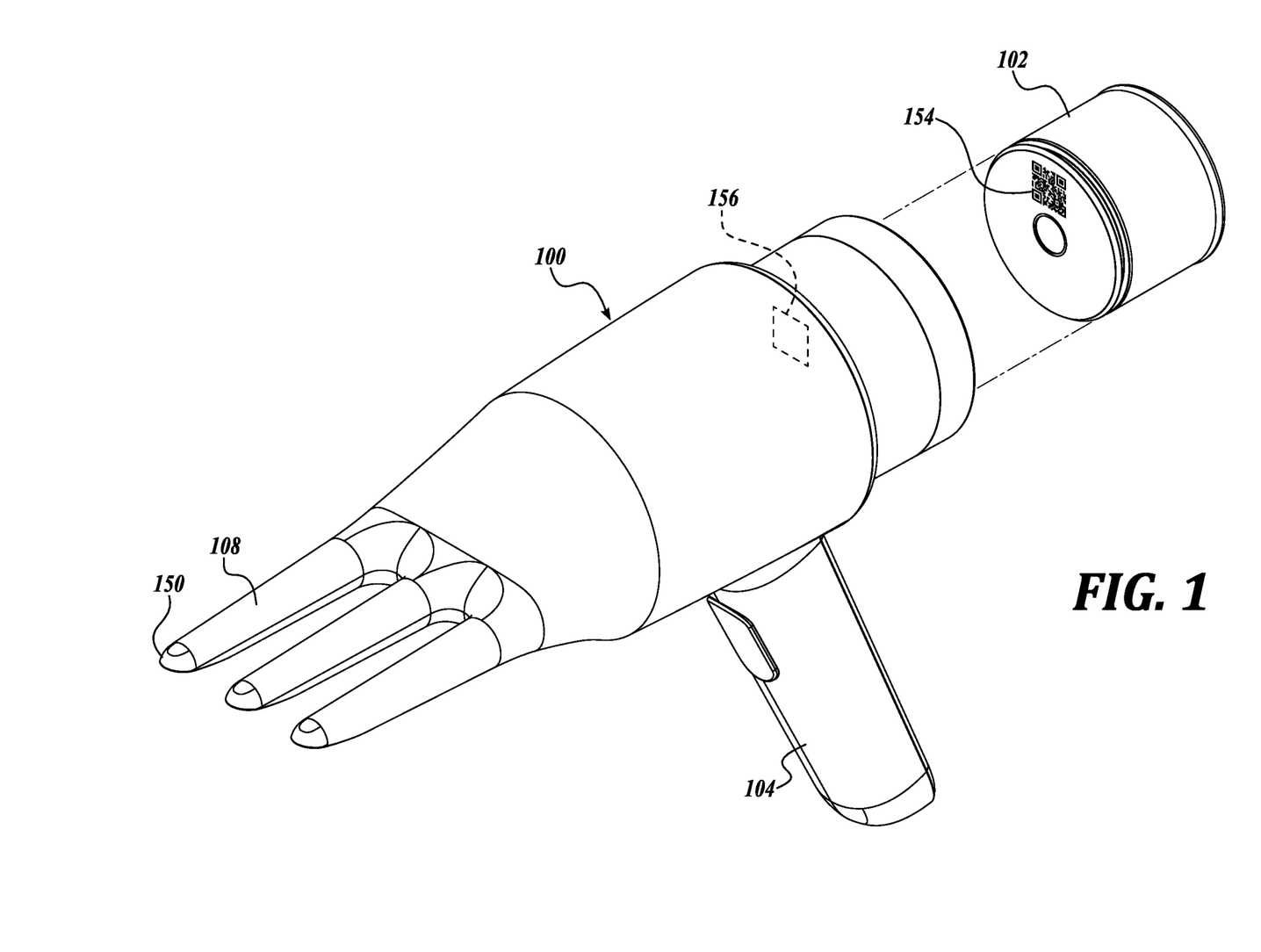
FIG. 1 is a diagrammatical illustration of a hair and scalp treatment device.

In one embodiment, the device 100 includes a formulation dispenser 112. In one embodiment, the formulation is stored in a replaceable or refillable cartridge 102. Cartridges 102 can be removable from the device 100 either to be re-filled or for disposal and replacement with a new full cartridge. Once emptied, a cartridge 102 can be replaced with a new cartridge filled with the same or different formulation or the cartridge can be refilled with the same or different formulation. As seen in FIG. 1, the cartridge 102 is inserted through the back side of the device 100. The cartridge 102 is connected to supply the scalp or hair formulation to the dispenser 112. In one embodiment, the device 100 can hold multiple cartridges, wherein each cartridge is filled with a different formulation, which can be dispensed to effect different treatments and to different regions of the scalp and hair.

In one embodiment, the cartridge 102 has a product identification tag 154 (FIG. 1) that can convey instructions for operation of the device 100 based on the specific formulation contained in the cartridge 102. The device 100 may include a product identification tag reader 156 (FIG. 1) capable of reading the product identification tag 154 and processing the encoded signals into instructions for operation and control of the device based on the particular formulation. Product identification tags, include for example, bar codes, 2-D bar codes, RFID, and the like. The product identification tag is encoded with machine readable signals that convey the device settings for the particular formulation. Different formulations may have different device settings. For example, the product identification tags can include the heat or vacuum setting, and the dispenser setting from liquid to fine, medium, or coarse droplets. Different formulations can also be used for treating different regions of the scalp and hair. Different formulations may also be used to provide different treatments to the scalp and hair. In one embodiment, the product identification tag identifies the formulation in the cartridge 102 as a containing charged particles, which controls the device 100 to turn on the electrostatic charger 152, and the product identification tag further determines the electrostatic setting, such as the particular voltage and the polarity of negative or positive.

The dispenser 112 can dispense one or more formulations through the tines 108 (or brush bristles or comb) as a fine mist or liquid. In one embodiment, dispensing the formulations as a mist or liquid, allows the device to also change the viscosity of the formulation being dispensed. In one embodiment, the dispenser 112 includes a compressor, pump, or ultrasonic wave generator to generate the mist from the formulation. In the case of a pump or compressor dispenser 112, such dispenser 112 causes air or the formulation to flow at a high velocity which propels the formulation through a fine nozzle designed for misting at the opening 130. In the case of a pump or compressor dispenser, a single dispenser 112 can be placed in the device 100. Then, the outlet of a compressor or pump dispenser 112 is routed through a system of conduits to each of the tines 108 and exits from the nozzle at the openings 130.

In an embodiment, the dispenser 112 is an ultrasonic wave nebulizer having an ultrasonic wave generator in contact with the formulation where the frequency of the ultrasonic waves is sufficient to produce the mist. An ultrasonic wave nebulizer also includes a "mesh" nebulizer that has a vibrating mesh just touching the surface of the formulation to create the mist. Either form of ultrasonic wave nebulizer can use a piezoelectric element.

In one embodiment, the device 100 includes an electrostatic charger 152. An electrostatic charger can produce a positive or negative charge at a targeted area of the scalp or hair or both. The electrostatic charger 152 is connected via an electrical conductor to an electrode 150 on the end of one or more tines 108. Suitable electrodes 150 are electrically conductive and may include, for example, copper, nickel, stainless steel, aluminum, or any alloys thereof. Electrodes 150 may be insulated from surrounding areas by an electrically insulating material, such as plastics, elastomers, and the like.

As the device 100 is operated, the electrostatic charger 152 can produce a positive or a negative charge on the scalp or hair or both to attract or repel formulations to the charged areas. In one example, positively charged areas are created by repelling electrons from the areas, and in another example, negatively charged areas are created by attracting electrons to the areas. Electrostatic charging may be conducted by contact electrocharging, induction electrocharging, and the like. In one example, the electrode 150 is connected to a high voltage source to induce the electrostatic positive or negative charges.

In another example, hair formulations are charged while passing by the charging electrode 150. Negatively charged hair formulation droplets are attracted towards the target which can be at a lower potential.

Figure 4:
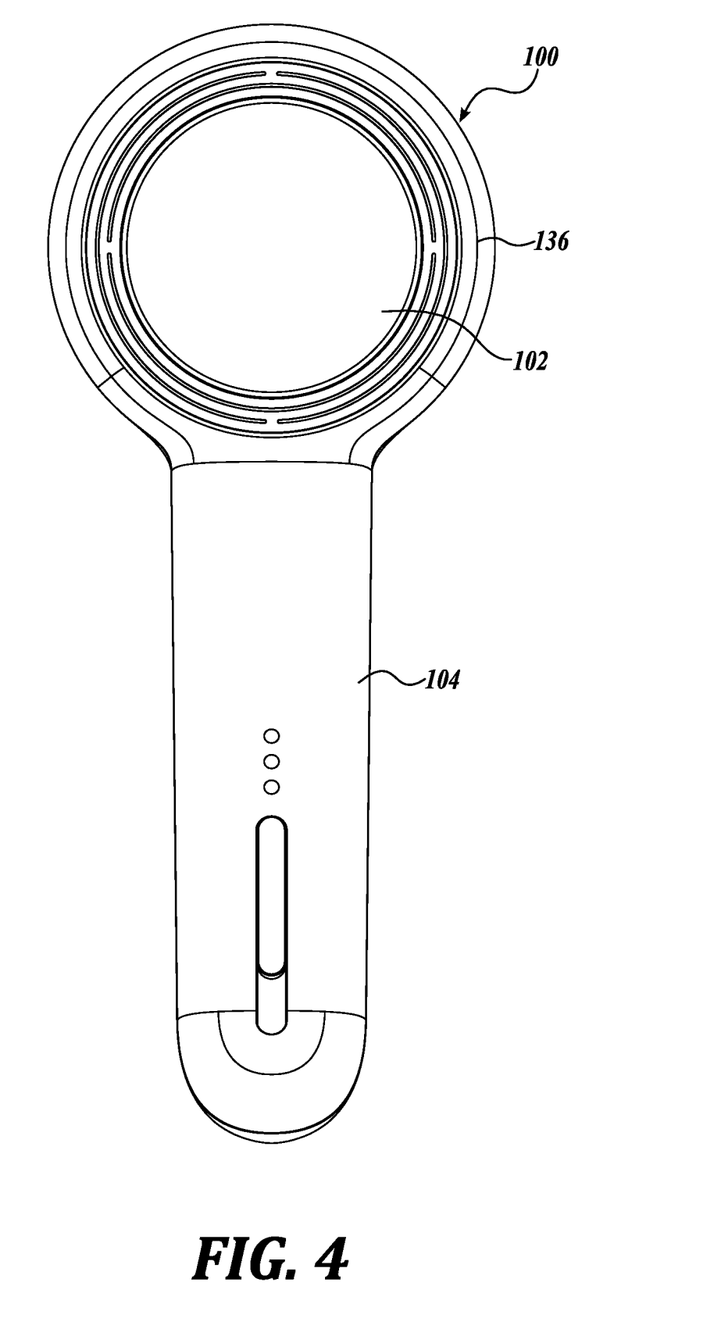
FIG. 4 is a diagrammatical illustration of a back view of the hair and scalp treatment device of FIG. 1.

In one embodiment, the device 100 includes a vacuum system 114 having a vacuum generating motor and collector. In one embodiment, a motor can be a variable speed motor. The motor induces a stream of air to enter through the openings 132 at the tines 108. The stream of air can carry the used formulation along with any debris and oils washed out of the hair by the formulation, which then gets captured by the collector, and the air is expelled out of the device 100. In one embodiment, the collector includes an annular vent 134 placed at the back of the device 100 and encircling the cartridge 102 (FIG. 4). The vent 134 allows the stream of air to exit the device 100, while the used and debris become trapped in the collector. In one embodiment, the collector is removable from the device 100 and is dishwasher safe so as to allow cleaning in a dishwasher. In one embodiment, the surface of the collector, which contacts the used formulation, is coated with a hydrophobic or hydrophilic material to facilitate cleaning of the collector.

In one embodiment, the device 100 includes a blower and heater system 114. In one embodiment, the device 100 may function as a hair dryer. The blower and heater system 114 may utilize the vacuum motor configured to rotate in the opposite direction. Where a vacuum is produced to take in air through the tines 108, the blower and heater system 114 is configured to blow air out through the tines 108. When operating as a blower, impeller vanes cause a stream of air to exit through the openings 132 at the tines 108. Before exiting, the stream of air can first be passed over a resistance heater coil. The temperature of the air can be increased or decreased by controlling the current that is applied to the heater coil. The air being expelled at the tines can enter the impeller vanes through the annular vent 134 placed at the back of the device 100.

In one embodiment, the device 100 includes a light treatment system 146. In one embodiment, the light treatment system includes one or more light-emitting diodes 146 (LEDs) capable of producing light over a broad range of the electromagnetic spectrum. In one embodiment, light therapy has been used on the scalp to treat a skin condition. In one embodiment, light therapy has been used to stimulate the cells of hair follicles. However, light therapy can have other benefits. In one embodiment, the light therapy is performed by light-emitting diodes 146 (LEDs) that are capable of producing electromagnetic energy in a wide range of wavelengths (either at individual wavelengths, such as a laser LED, or at multiple wavelengths in a wide range). The intensity of the light produced by the LED can be varied by controlling the current, for example.

In one embodiment, the LEDs 146 include one or more Group III-V (GaAs) based LEDs that are capable of emitting electromagnetic radiation at wavelengths in a range spanning from green visible light to near infrared. In one embodiment, the LEDs 146 include one or more Group III-nitride blue LED solid state emitters that are capable of emitting electromagnetic radiation at wavelengths in a range spanning from ultraviolet to blue visible light.

In one embodiment, the wavelength output of the LEDs 146 includes one or more gallium-indium-nitrogen (GaInN) LEDs that have a wavelength output of about 360-370 nm. In other embodiments, the LEDs 146 emit electromagnetic energy in a range of wavelengths from about 200 nm to about 2000 nm, which includes wavelengths in the ultraviolet range (about 350 nm) and near infrared (about 1200 nm).

In one embodiment, the use of different LEDs that produce different wavelength light can be used to provide for different treatments to the scalp and hair.

In one embodiment the device 100 includes a haptic system 158. The haptic system may include a vibratory massager. In one embodiment, a haptic vibrating massager can include an electric motor that rotates an eccentrically placed weight that produces vibrations according to the speed of rotation. In one embodiment, the vibrating haptic massager can include an electromagnetic coil and permanent magnet that produces vibrations according to the cycles of the electricity source. Additionally, other technologies may be used in the haptic system 158 to produce a type of haptic actuation or sensation producing affects including ceramic piezoelectric actuators, Shape Memory Alloy and Shape Memory Polymer actuators, electrostatic forces, electroactive polymer actuators, piezoelectric motor actuators, and pneumatic actuators.

In one embodiment, the device 100 includes one or more sensors. In one embodiment, one or more sensors are used for measuring one of device distance in relation to scalp or hair, device speed, or device direction. In an embodiment, speed and direction are used for detecting a back-and-forth "brushstroke" technique. In one embodiment, the device 100 includes a contact sensor 160. A contact sensor 160 can indicate whether or not the tines 108, or brush, or comb, are in physical contact with skin and hair. In one embodiment, the device 100 includes a proximity sensor 162. A proximity sensor 162 can indicate the distance from the sensor to the surface of the skin and hair. In an embodiment, the contact sensor 160 and proximity sensor 162 can be placed at or near the end tip of one, more than one, or all tines 108 (or brush bristles or comb teeth). In one embodiment, the device includes one or more accelerometers 164. In one embodiment, the accelerometers 164 are two-axes and three-axes accelerometers that function to determine device 100 orientation or device 100 position in relation to the head and hair. For example, the device 100 is generally held in a different orientation when being used on the top of the head as opposed to the back, and the right and left sides. The two-axes and three-axes accelerometers 164 are used to track the orientation of the device 100 from which position can be determined. Although, the accelerometers 164 are illustrated on the tines 108, the accelerometers can be placed anywhere on the device 100.

In one embodiment, the contact sensor 160 includes open or short detectors or dielectric sensors. An open detector can refer to an open circuit detector for detecting a broken (open) continuity in an electrical transmission. A short detector can refer to detection of low electrical resistance. A dielectric sensor is also referred to as a capacitance detector which can detect a change in dielectric permittivity. In one embodiment, the contact sensor 160 may be a sensor that detects contact or no contact of an individual tine 108 (or brush bristle or comb tooth). In one embodiment, the contact sensor 160 may indicate the amount of contact. An example of a contact sensor that can detect an amount of contact is a piezoelectric sensor.

In one embodiment, the proximity sensor 162 may be an optical sensor, such as an infrared sensor or camera or both camera and infrared sensors. In one embodiment, the infrared or camera sensors or both can be positioned at various locations throughout the device 100. In one embodiment, the camera may be a semiconductor integrated circuit that converts light into images, such as a charge coupled device (CCD) or pixel sensors. An infrared sensor detects heat which is inversely proportional to the distance of the device from a heat source. However other examples of proximity sensors may be employed as well, such as a capacitive, ultrasonic, or Doppler sensors.

In one embodiment, the accelerometers 164 function to determine the device 100 position (or location in relation to the head), device 100 orientation, and motion of the device 100. In one embodiment, accelerometers 146 may be used in combination with other sensors, including a geomagnetic sensor (i.e., compass) and a gyroscope. A gyroscope is a sensor that detects angular velocity about three axes and is able to detect the rotation of an object. In addition, the geomagnetic sensor is able to ascertain the heading in which the device 100 faces.

In one embodiment, the device 100 includes a controller 148. In one embodiment, the controller 148 is a digital device. The controller 148 may include one or more hardware circuits connected on a printed circuit board, or all of circuits may exist on a single chip. The controller 148 may include at least a microprocessor core and a memory. The hardware can be designed for use in small hand operated devices. The microprocessor may be implemented as multiple processors cooperatively working in parallel and series to perform instructions according to pre-programmed logic.

The controller 148 receives signals from sensors, such as the contact sensor 160, proximity sensor 162, and accelerometer(s) 164. Sensors 160, 162, 164 may include circuits that provide digital signals for storage and processing by the controller 148. In one embodiment, one or more sensor may send analog signals that are converted to digital signals by an analog-to-digital converter circuit before storage and processing by the controller 148.

The controller 148 may perform various operations based on one or more of the signals provided by the sensors. Additional information may also be available to the controller 148 such as clocks to count the passage of time and past data from the sensors.

The controller 148 converts and interprets the signals from the sensors to mean a spatial condition of the device 100, for example, the signals can be interpreted to indicate contact or no contact with the device 100, distance from device 100, and location of device 100 in relation to the scalp and hair. Then, the controller 148 will perform certain pre-programmed instructions based on one or more of the signals. The instructions can be encoded in hardware or software. The instructions relate to whether and how to change the operation of one or more of the treatment systems based on the signals from the sensors.

In an embodiment, each treatment system 122, 152, 114, 144, and 146 has a treatment protocol that specifies what treatment should be provided based on the real-time spatial conditions of the device 100. In this manner, the controller 148 sends command signals to the treatment system 122, 152, 114, 144, and 146 to adjust the treatment as the user moves the device 100 to different regions of the scalp and hair. The controller 148 bases its instructions on the current (in real-time) detected spatial conditions of the device 100. Spatial conditions can relate to contact, distance, and location and orientation of the device 100 from the hair and scalp. Treatment protocols can be provided as any tabular data or functions that correlate a region or distance to scalp or hair with a treatment condition. For example, a hair dryer can be controlled to vary the air temperature proportional to the distance the device 100 is moved away from the hair. In such example, the treatment protocol would be air temperature as a function of distance or in tabular data, a table having a row for each temperature setting and a column for each distance setting, where the intersection of rows and columns provides the treatment temperature for the spatial condition (distance in this example). Treatment protocols for other treatment devices can be set up in a similar manner and based on other spatial conditions.

Instructions corresponding to each treatment protocol can be stored in any type of computer-readable medium or computer storage device and be stored on and executed by one or more microprocessors. Instructions may be stored in a high-speed memory such as a EEPROM, Flash memory, RAM, or other programmable non-volatile memory. Instructions can be written in a programming language, such as C, C++, COBOL, JAVA™ PHP, Perl, HTML, CSS, JavaScript, VBScript, ASPX, Microsoft .NET™, Go, and/or the like.

A treatment protocol for the dispenser 122 based on spatial conditions of the device 100 may include, for example, changing the character of the formulation being dispensed from being liquid to a mist depending on whether the formulation is being directed at the scalp or into the hair, or direction of the formulation being sprayed can be changed or stopped altogether by sensing the position of the device 100 in relation to the hair or not sensing any hair. The treatment protocol also considers the type of formulation to be dispensed, i.e., whether the formulation is a skin or scalp treatment or a hair treatment. When the device 100 holds more than one cartridges, the device 100 can be configured to dispense a different formulation based on detecting the device is moved from one location to another location where the treatment protocol calls for a different formulation to be dispensed at the second location.

A treatment protocol for the electrostatic charger 152 based on spatial conditions of the device 100 may include, changing the electrostatic parameters based on whether the device 100 is in contact with or within a maximum distance in relation to the scalp (skin) or hair.

A treatment protocol for the vacuum 114 based on spatial conditions of the device 100 may include, reducing the force of the vacuum based on contact with the skin or scalp, increasing the vacuum the further the device 100 is moved away from the skin or scalp.

A treatment protocol for the blower heater 144 based on spatial conditions of the device 100 may include, reducing the force of the air and temperature based on contact with the skin or scalp and increasing the blowing force and temperature the further away the device 100 is moved away from the skin or scalp.

A treatment protocol for the light system 146 based on spatial conditions of the device 100 may include, turning on certain light therapies based on contact with the skin or contact with the hair, increase or decrease the power of the light therapy based on distance, or turn off the light therapy when no contact or a distance is exceeded beyond which light therapy is ineffective. In one embodiment, the different light emitting diodes may be illuminated based on detecting the device is moved from one location to another, and the treatment protocol calls for the different LEDs based on the second location.

Figure 7:
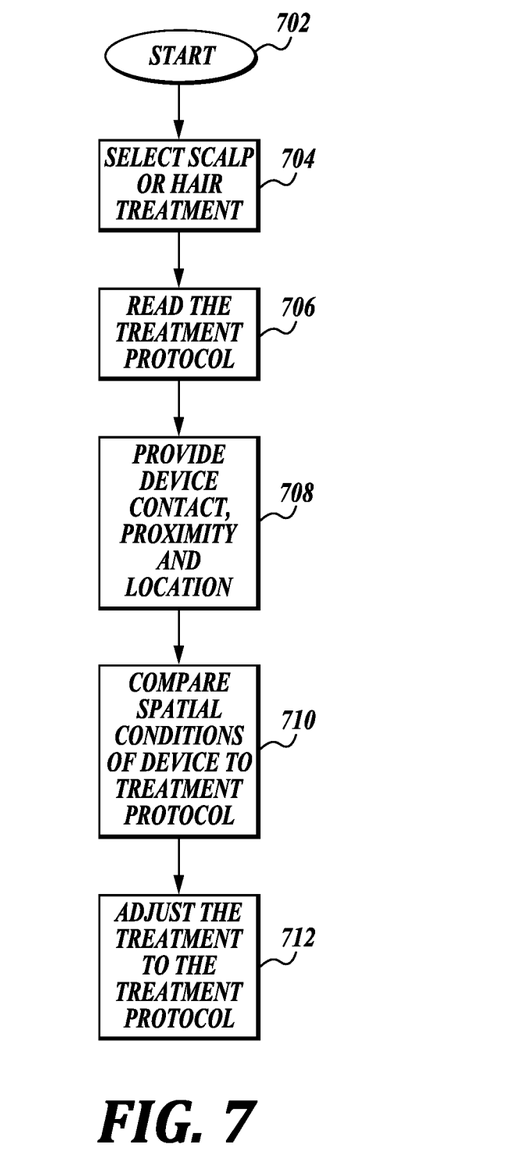
FIG. 7 is a flow diagram of a method of the operation of the device of FIG. 1.

FIG. 7 is a flow diagram illustrating one embodiment of operation of the device 100 that changes or adjusts the operation of a hair or scalp treatment system based on the spatial conditions of the device 100.

In one embodiment, in the start block 702, the device 100 may turn itself on when the device 100 detects that it has been picked up by a user by a signal from the accelerometer 164. From block 702, the device enters block 704.

In one embodiment, when the device 100 is used for more than one treatment, i.e., the device 100 has more than one treatment system 112, 152, 114, 144, 146, the user may select the treatment system in block 702. If the device 100 has a single treatment system, block 702 can be omitted. From block 704, the device 100 enters block 706.

In block 706, the device 100 reads the treatment protocol based on the selected treatment system. Here, "read" can mean to access or to store the treatment protocol in a manner that can be used by the controller 148. The treatment protocol can be stored in a memory of the controller 148. A treatment protocol specifies the treatment delivered by the treatment system based on the changing spatial conditions of the device. Spatial conditions can mean one or more condition to indicate contact or no contact with the device 100, distance from device 100, and location of device 100 in relation to the scalp and hair. A treatment system 112, 152, 114, 144, 146 may change the treatment being delivered by the treatment system in real-time based on device 100 contact, device 100 distance, and device 100 location relative to the scalp or hair. From block 706, the device enters block 708.

In block 708, the device 100 receives the sensor data in real-time and interprets the data to determine the spatial conditions of the device 100. For example, the spatial conditions that can be determined from the sensors include contact or no contact with device 100, device 100 distance to scalp and hair, and location of the device 100 in relation to the scalp or hair. From block 708, the device 100 enters block 710.

In block 710, the device 100 compares the current spatial conditions of the device 100 to the pre-programmed treatment protocol. From block 710, the device 100 enters block 712.

In block 712, the device 100 adjusts the treatment system according to the treatment protocol for the current spatial conditions of the device 100. For example, if the selected treatment system is a formulation dispenser 112, the treatment protocol for the dispenser 112 may use a different setting or formulation for contact on the scalp (for hair roots) and a different dispensing setting or formulation the further away the device 100 is moved from the scalp. For example, the formulation can be dispensed as a liquid when the device 100 is in contact with the scalp, and with increasing distance from the scalp, the dispenser 112 reduces the amount or applies formulation as a finer and finer mist. The treatment protocol for the blower and heater 144 may call for minimum heat and airflow setting when contact with the scalp is detected, and the treatment protocol may call for temperature and airflow to gradually increase with increasing distance of the device 100 from the scalp or hair. The protocol for the light treatment system 146 may call for the LEDs only turn on when the device 100 is in contact with the scalp and turn off if no contact or a distance increases beyond the effective range of the light therapy. A treatment protocol for the LEDs may require that different wavelength LEDs are illuminated depending on the region of the scalp detected by the device. The instructions to change the treatment system come from the controller 148 which is in communication with each of the treatment systems.

When the device 100 is set down, such as no movement is detected for a pre-determined amount of time, as determined by the accelerometers, the device 100 may reduce power or be in a stand-by mode.

Use of the device 100 minimally impacts the hair style, the overall shape of the device 100 is familiar to other hair appliances, such as a hair dryer, leading to simple intuitive use of the device 100. Further, the device 100 does not require hand contact with hair formulations. The device 100 adds functionality to make operation more simple, tailor the treatment to the specific spatial location of the device will minimize waste and avoid dispersing mists into air where they may be inhaled.

While illustrative embodiments have been illustrated and described, it will be appreciated that various changes can be made therein without departing from the spirit and scope of the invention.

The embodiments of the invention in which an exclusive property or privilege is claimed are defined as follows:

1. A device, comprising:
   a treatment system including an air blower and heater to treat scalp or hair;
   one or more sensors configured to detect device distance to scalp or hair;
   one or more contact sensors configured to detect device contact with the scalp;
   a controller configured to send instructions to adjust the treatment system based on the distance of the device to the scalp or hair, wherein the heater and air blower increase a force and temperature of blowing air with increasing distance and decrease the force and temperature of the blowing air with decreasing distance;
   the device includes a handle connected at an obtuse angle to a front end of the device, the handle extending in a top to bottom plane, the front end including three tines, wherein the three tines are placed in a side to side plane, wherein a front end of each tine includes a truncated rounded shape, the truncated rounded shape including a chamfered section being a flat area on a bottom facing side of each tine and a rounded shape on top of each tine, wherein the flat area of each tine includes an opening;
   a dispenser that dispenses a formulation through the openings in the flat areas of the tines, and the controller controls the dispenser to reduce an amount of the formulation dispensed with increasing distance of the device with the scalp or hair; and
   the controller further controls dispensing the formulation as a liquid when contact with the scalp is detected and dispensing the formulation as a mist when no contact with the scalp is detected.

2. The device of claim 1, wherein the treatment system includes a replaceable or refillable cartridge, wherein the device accepts cartridges having different formulations.

3. The device of claim 1, wherein the treatment system further includes an electrostatic charger.

4. The device of claim 1, wherein the treatment system further includes a vacuuming system.

5. The device of claim 1, wherein the treatment system further includes a light therapy system.

6. The device of claim 1, wherein the treatment system further includes a haptic massager system.

7. The device of claim 1, comprising a contact sensor configured to detect contact of the device with scalp or hair, the contact sensor is selected from an open detector, a short detector, and a dielectric sensor.

8. The device of claim 1, comprising a camera or infrared sensor or both camera and infrared sensors to detect device distance in relation to scalp or hair.

9. The device of claim 1, comprising a controller having instructions stored therein to perform steps, including:
   accessing a treatment protocol for a treatment system, the treatment protocol specifies a treatment based on the distance of the device in relation to the scalp or hair.

10. The device of claim 1, comprising a controller having instructions stored therein to perform steps, including:
    commanding the treatment system to adjust the treatment based on the distance of the device in relation to the scalp or hair.

11. A method for treating hair or scalp with the device of claim 1 including a treatment system and a controller having instructions stored therein to perform steps, the method comprising:
    with the controller, accessing a treatment protocol for the treatment system, wherein the treatment protocol specifies a treatment based on spatial conditions of the device;
    with the controller, interpreting signals from one or more sensors into a distance of the device in relation to the scalp or hair;
    with the controller, comparing the distance of the device to the treatment protocol; and
    with the controller, commanding the treatment system to adjust the treatment to the treatment protocol, the controller controls the dispenser to reduce an amount of the formulation dispensed with increasing distance of the device with the scalp or hair.

12. The method of claim 11, further comprising, with the controller, commanding the treatment system to change a direction of dispensing a formulation or a pattern of dispensing the formulation.

13. The method of claim 11, further comprising, with the controller, commanding the treatment system to change the amount or viscosity of formulation being dispensed.

14. The method of claim 11, further comprising, with the controller, commanding the treatment system to dispense different formulations based on detecting the device is moved from one location to another.

15. The method of claim 11, further comprising, with the controller, commanding that treatment system to illuminate different light emitting diodes based on detecting the device is moved from one location to another.

* * * * *